United States Patent
Pearson

(10) Patent No.: US 12,022,970 B2
(45) Date of Patent: Jul. 2, 2024

(54) SYSTEMS AND METHODS FOR DISPENSING ITEMS SUCH AS SACRAMENTAL ELEMENTS

(71) Applicant: Michelle Pearson, Merrillville, IN (US)

(72) Inventor: Michelle Pearson, Merrillville, IN (US)

(73) Assignee: MPB Essential Technology, Inc., Merrillville, IN (US)

(*) Notice: Subject to any disclaimer, the term of this patent is extended or adjusted under 35 U.S.C. 154(b) by 487 days.

(21) Appl. No.: 17/244,048

(22) Filed: Apr. 29, 2021

(65) Prior Publication Data

US 2022/0346584 A1 Nov. 3, 2022

(51) Int. Cl.
*A47G 33/00* (2006.01)
*A21D 15/06* (2006.01)
*A23L 2/50* (2006.01)
*A61L 2/10* (2006.01)
*A61L 2/24* (2006.01)
*A61L 2/26* (2006.01)
*B65D 83/04* (2006.01)
*C12H 1/16* (2006.01)

(52) U.S. Cl.
CPC ............ *A47G 33/00* (2013.01); *A21D 15/06* (2013.01); *A23L 2/50* (2013.01); *A61L 2/10* (2013.01); *A61L 2/24* (2013.01); *A61L 2/26* (2013.01); *B65D 83/0409* (2013.01); *C12H 1/165* (2013.01); *A23V 2002/00* (2013.01); *A61L 2202/11* (2013.01); *A61L 2202/121* (2013.01); *A61L 2202/122* (2013.01); *A61L 2202/14* (2013.01); *A61L 2202/23* (2013.01)

(58) Field of Classification Search
CPC ....................................................... A47G 33/00
See application file for complete search history.

(56) References Cited

U.S. PATENT DOCUMENTS

| 6,253,669 B1 | 7/2001 | Bourque |
| 11,339,061 B2 * | 5/2022 | Hobson ................... F24S 60/30 |
| (Continued) |

FOREIGN PATENT DOCUMENTS

KR          102085326          3/2020

OTHER PUBLICATIONS

International Search Report and Written Opinion for International Application No. PCT/US2021/030050, dated Aug. 10, 2021, 8 pages.

*Primary Examiner* — Gene O Crawford
*Assistant Examiner* — Ayodeji T Ojofeitimi
(74) *Attorney, Agent, or Firm* — Hartman Global IP Law; Gary M. Hartman; Domenica N. S. Hartman

(57) ABSTRACT

Systems and methods for dispensing items utilizing a housing having a compartment configured to store a quantity of items, a dispensing device configured to dispense at least one of the items from the housing to an individual, an activation device configured to activate the dispensing device to dispense the at least one item from the housing in response to an interaction with the individual, an outlet in the housing through which the items may be individually dispensed from the housing by the dispensing device, and one or more light sources that emit UV-C radiation within the housing and irradiate exterior surfaces of the items or packaging of the items with the UV-C radiation. Methods utilizing the system may be used to dispense items, such as sacramental elements for Communion.

18 Claims, 8 Drawing Sheets

(56) References Cited

U.S. PATENT DOCUMENTS

| | | |
|---|---|---|
| 2003/0094345 A1 | 5/2003 | Munini |
| 2007/0137726 A1 | 6/2007 | Yan |
| 2009/0148358 A1* | 6/2009 | Wind ........................ A61L 2/10 422/186.3 |
| 2015/0217011 A1* | 8/2015 | Bettles ...................... A61L 2/10 250/435 |
| 2019/0073648 A1 | 3/2019 | Salvucci et al. |

* cited by examiner

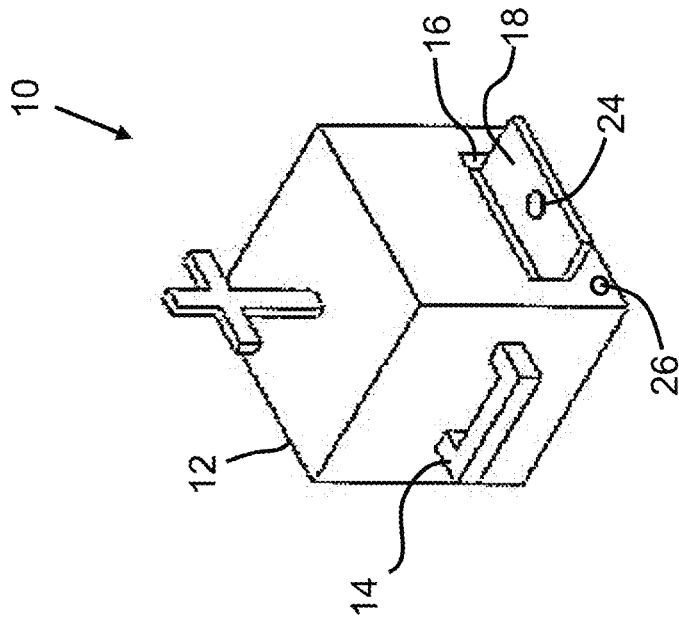
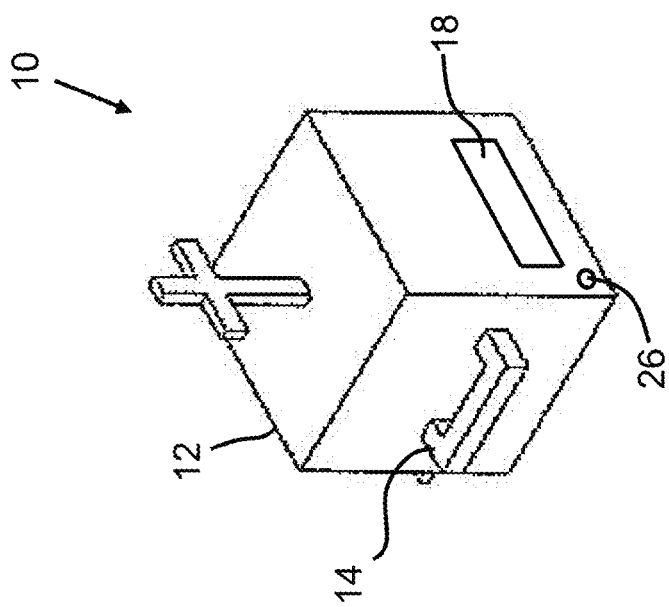

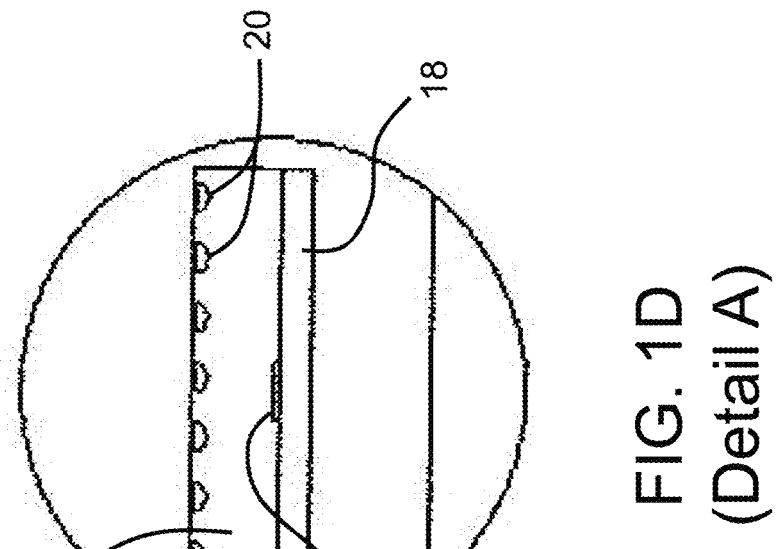
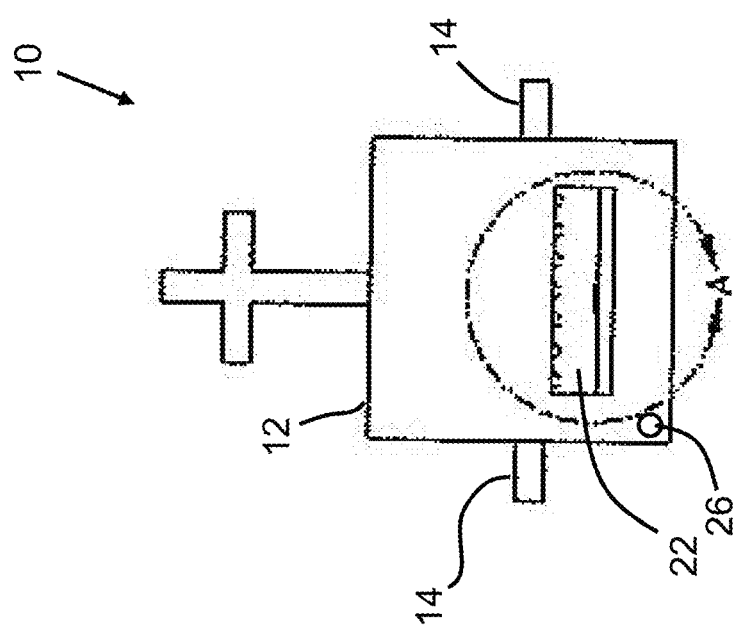
FIG. 1D (Detail A)
FIG. 1C

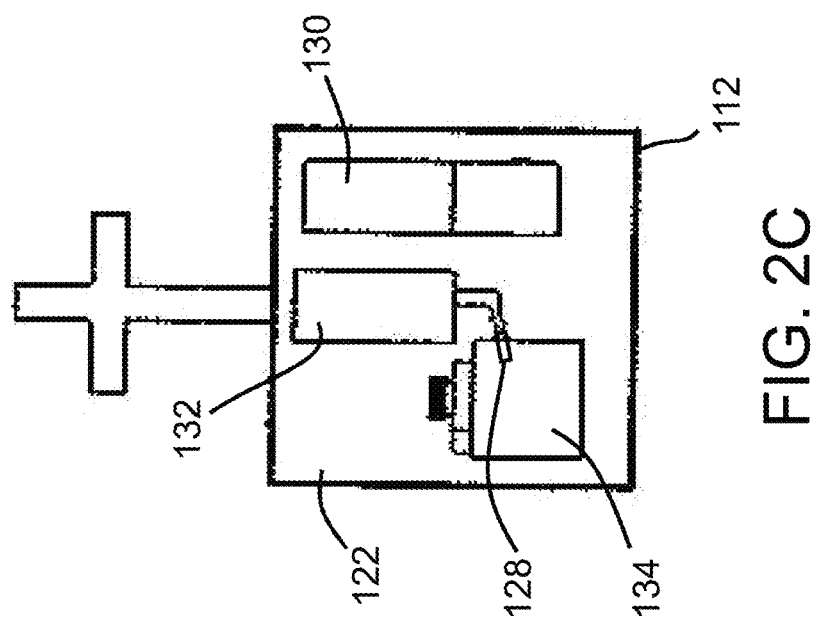

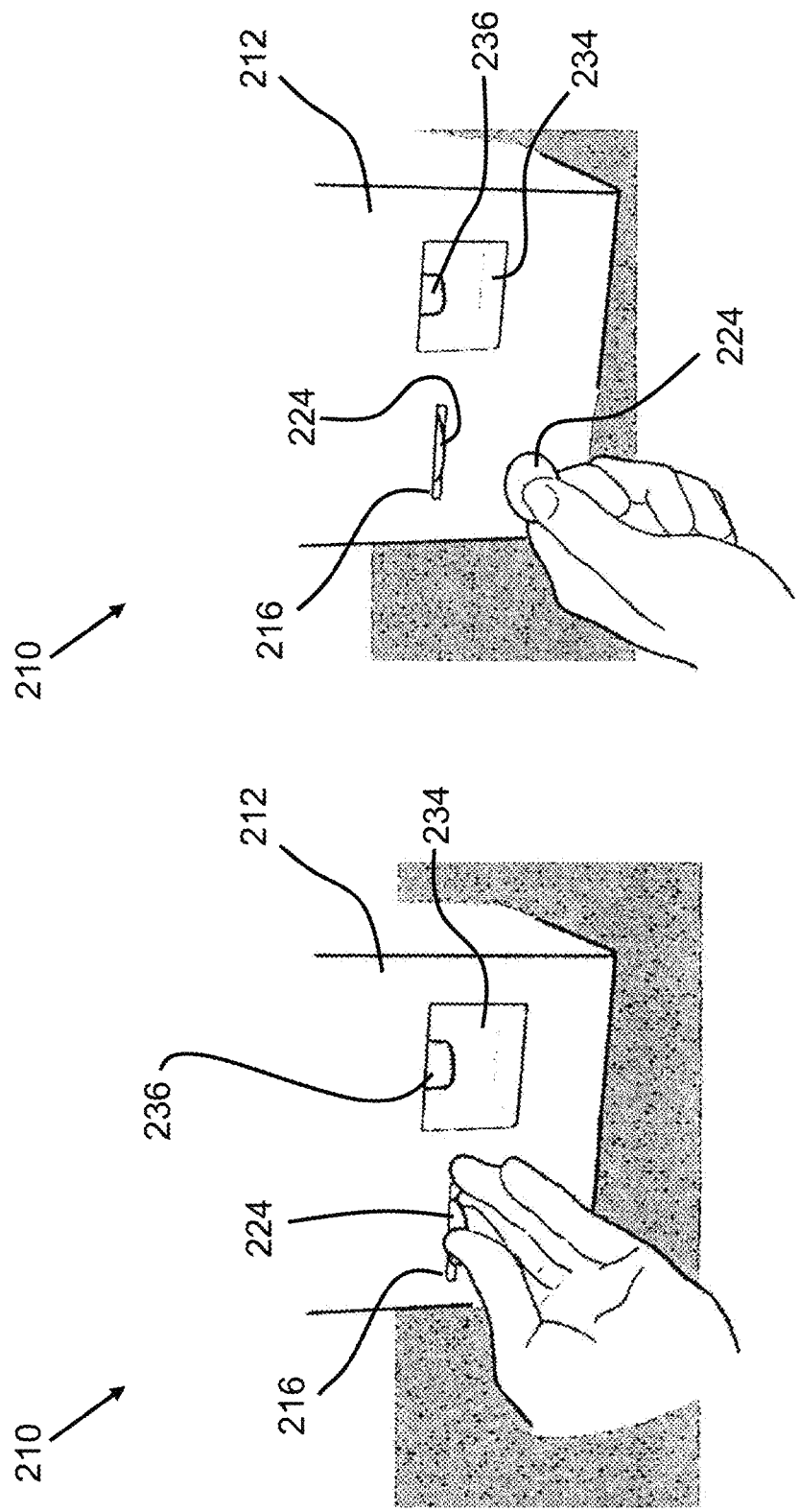

(Section A-A)

SYSTEMS AND METHODS FOR DISPENSING ITEMS SUCH AS SACRAMENTAL ELEMENTS

CROSS REFERENCE TO RELATED APPLICATIONS

This application claims the benefit of U.S. Provisional Application No. 63/018,150, filed Apr. 30, 2020, the contents of which are incorporated herein by reference.

BACKGROUND OF THE INVENTION

The present invention generally relates to devices and methods for dispensing items. The invention particularly relates to systems and methods of dispensing solid, liquid, and/or prepackaged items, as nonlimiting examples, sacramental bread, sacramental wine, items representative of bread and wine (e.g., communion wafers or grape juice), and packaging containing such items.

The Christian rite of Communion is performed by worshipers (Communicants) during Christian religious ceremonies. The rite involves an individual consuming small portions of sacramental bread (leavened or unleavened) and sacramental wine which have been consecrated on an altar (or a Communion table). Certain substitutes may be used for the traditional bread and wine, such as non-alcoholic grape juice. Such items (individually and collectively referred to herein respectively as a "sacramental element" and as "sacramental elements") consumed during this rite are commonly provided to Communicants in individual-sized containers such that each individual consumes a predetermined amount of each sacramental element. For example, Communicants may individually obtain a wafer and a small cup of wine from a communion table, from a tray passed among the Communicants, or directly from a congregation leader. These practices may have various disadvantages such as accidental spillage of the sacramental elements, material waste, or the passing of infectious agents (e.g., viruses, bacteria, etc.) among the Communicants.

In view of the above, it can be appreciated that it would be desirable if systems and methods were available for distributing sacramental elements to Communicants that reduce the risk of waste and promote sanitation.

BRIEF DESCRIPTION OF THE INVENTION

The present invention provides systems and methods suitable for dispensing solid, liquid, and/or prepackaged items, such as individual servings of sacramental elements to Communicants, preferably in a manner that reduces waste and promotes sanitation and efficiency.

According to one aspect of the invention, a system is provided that includes a housing having a compartment therein configured to store a quantity of items, a dispensing device configured to dispense at least one of the items from the housing to an individual, an activation device configured to activate the dispensing device to dispense the at least one item from the housing in response to an interaction with the individual, an outlet in the housing through which the items may be individually dispensed from the housing by the dispensing device, and one or more light sources that emit UV-C radiation within the housing and irradiate exterior surfaces of the items or packaging of the items with the UV-C radiation.

According to another aspect of the invention, a method is provided for distributing items that includes providing a system comprising a housing having a compartment therein configured to store a quantity of the items, sensing an interaction between an individual and an activation device of the system, activating a dispensing device of the system to dispense at least one of the items from the housing through an outlet of the housing in response the interaction between the individual and the activation device, and irradiating exterior surfaces of the items or packaging of the items with UV-C radiation emitted from one or more light sources within the housing.

Technical effects of the system and method described above preferably include the ability to efficiently dispense solid, liquid, and/or prepackaged items, such as sacramental elements to Communicants, potentially with a reduced likelihood of spillage or contamination thereof, and thereby preferably reducing waste and the spread of infectious agents.

Other aspects and advantages of this invention will be appreciated from the following detailed description.

BRIEF DESCRIPTION OF THE DRAWINGS

FIGS. 1A, 1B, 1C, and 1D represent various views of a first nonlimiting embodiment of a dispensing system in accordance with certain aspects of the invention.

FIG. 2C represents a cutaway rear view of the dispensing system of FIGS. 2A and 2B showing certain nonlimiting components therein.

FIGS. 3A and 3B represent partial perspective views of a third nonlimiting embodiment of a dispensing system and a method for its use in accordance with certain aspects of the invention.

DETAILED DESCRIPTION OF THE INVENTION

Figure 2B:
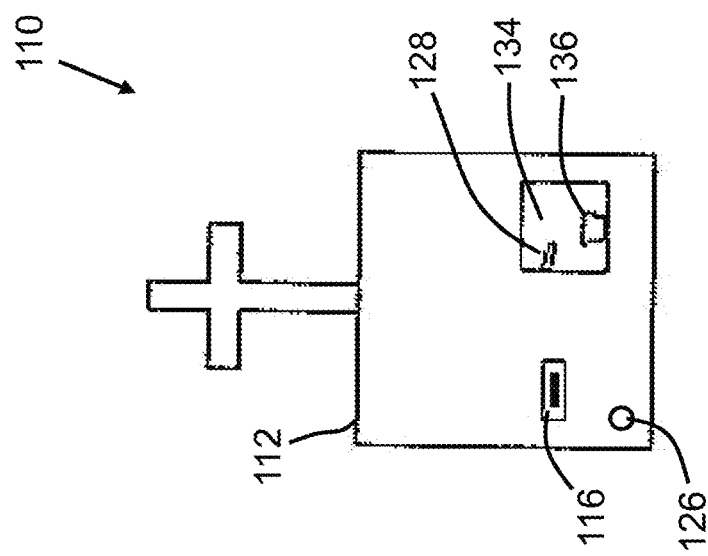
FIGS. 2A and 2B represent perspective and front views of a second nonlimiting embodiment of a dispensing system in accordance with certain aspects of the invention.

The intended purpose of the following detailed description of the invention and the phraseology and terminology employed therein is to describe what is shown in the drawings, which include the depiction of one or more nonlimiting embodiments of the invention, and to describe certain but not all aspects of the embodiments depicted in the drawings. The following detailed description also identifies certain but not all alternatives of the depicted embodiments. Therefore, the appended claims, and not the detailed description, describe what is believed to be one or more aspects of the invention.

FIGS. 1 through 6 represent nonlimiting embodiments of systems and methods of using these systems for dispensing sacramental elements therefrom, for example, for use during Communion. The systems each include a housing having a compartment therein configured to store a quantity of solid or liquid sacramental elements such as sacramental wine, sacramental bread, and/or substitutes therefor. The systems are configured to manually or automatically dispense the sacramental elements from the housings to an individual during Communion, preferably in consistent, predetermined quantities (e.g., single servings) and preferably in a manner that reduces waste and promotes sanitation. The sacramental elements may be dispensed alone or in various packaging materials.

FIGS. 1A, 1B, 1C, and 1D represent aspects of a first embodiment of a system 10 for dispensing sacramental elements. The system 10 includes a housing 12 configured to store a quantity of at least one solid sacramental elements 24 (e.g., a communion wafer) within a compartment 22 (FIGS. 1C and 1D) enclosed within the housing 12. In certain embodiments, the housing 12 may be closed or sealed to preserve and protect the solid sacramental elements stored therein. The solid sacramental elements 24 may be stored and dispensed with or without individual packaging.

The system 10 includes a dispensing device (not shown) within the compartment 22 that is configured to controllably dispense a predetermined quantity of the solid sacramental element 24. The dispensing device dispenses the solid sacramental element 24 in response to an individual's interaction with an activation device 26 of the system 10 (schematically represented in FIGS. 1B and 1C). The device 26 may take various forms, and as such interactions with the device 26 may entail various actions such as but not limited to direct, physical contact between the individual and a mechanical component such as an electrical or mechanical button, switch, or touchscreen digital display interface on the exterior of the housing 12, remote interaction by the individual with a wireless element of a wireless technology signal or network associated with the housing 12, or physical proximity of the individual to the housing 12 detected by a proximity sensor associated with the housing 12. The system 10 may store a single type or multiple types of sacramental elements 24. In embodiments that include multiple types of sacramental elements 24, the system 10 may include features or activation devices configured to allow an individual to select one of the desired types of sacramental elements to be dispensed.

The system 10 includes a cover panel 18 configured to close or otherwise cover an outlet or slot 16 in the housing 12 that provides access to the compartment 22 within the housing 12. Upon interaction with the activation device 26, the cover panel 18 opens to uncover or reveal the slot 16, remains open as the dispensing device dispenses one or more sacramental elements 24 through the slot 16, and then closes to cover the slot 16 after the sacramental element(s) 24 have been received by the individual. In certain embodiments, the cover panel 18 may be manually opened thereby activating the activation device 26 and causing the solid sacramental element 24 to be dispensed.

In the embodiment of FIGS. 1A and 1B, the cover panel 18 opens by pivoting outward along a lower edge thereof to uncover the slot 16 and provide access to the compartment 22 within the housing 12. The cover panel 18 may remain in an open position, for example, a generally horizontal position, as the sacramental element 24 is dispensed. The dispensing device dispenses a solid sacramental element 24, in this example a single communion wafer, through the slot 16 such that it is deposited on an upper surface of the cover panel 18. In this embodiment, the cover panel 18 acts as a serving tray that supports the sacramental element 24 until retrieved by an individual. After retrieval of the sacramental element 24, the cover panel 18 may be manually closed to cover the slot 16 or may be configured to automatically close without assistance, for example, in combination or cooperation with the activation device 26. The cover panel 18 may promote the protection and preservation of any perishable sacramental elements contained within the compartment 22.

In preferred embodiments, the system 10 includes means for sanitizing the sacramental elements 24 stored in the compartment 22, packaging of the sacramental elements 24, certain portions including the upper surface of the cover panel 18, and/or other internal components and surfaces of the housing 12. Nonlimiting methods of sanitizing the contents of the housing 12 may include exposure to elevated temperatures and/or pressures (e.g., autoclaving), steam, electron beam radiation, certain gaseous fluids (e.g., ozone), or certain liquid fluids (e.g., alcohol). In FIG. 1D, the system 10 is schematically represented as being equipped with one or more light sources 20 capable of emitting ultraviolet (UV) radiation within the housing 12 for the purpose of sanitizing the contents of the compartment 22. Preferably, the light sources 20 emit wavelength ranges that include ultraviolet C (UV-C or short-wave UV) having wavelengths of 100-280 nm, more preferably 200-280 nm, which is believed to be particularly effective as a germicide capable of inactivating certain infectious agents. In this manner, the contents of the compartment 22 may be continuously or selectively sanitized. The light sources 20 may include various types of lamps, such as but not limited to compact fluorescent lights, light-emitting diodes (LEDs), or a combination thereof.

In addition to the light sources 20, the system 10 may include various other means for promoting irradiation of the contents of the housing 12 by the light emitted by the light sources 20. For example, the system 10 may include polished or reflective surfaces within the compartment 22. Further, certain components within the housing 12 may be perforated or slotted to allow for the emitted light to travel therethrough. In certain embodiments, the housing 12 may be configured such that light emitted from the light sources 20 does not leak from (i.e., is not emitted through) the slot 16 when the cover panel 18 is open.

The system 10 may include control systems for operating the light sources 20 in various manners. For example, such control systems may be configured to automatically deactivate the light sources 20 when the cover panel 18 opens and automatically activate the light sources 20 when the cover panel 18 closes. The control systems may manage durations and intensity of the UV radiation emitted by the light sources 20. Such control systems may be operated based on predetermined programing or a timer or schedule, may be controlled by an individual via an activation device or controls such as, but not limited to, an electrical or mechanical button, switch, or touchscreen digital display interface, remote connection via a wireless technology signal or network, or in response to a physical proximity of the individual detected by a sensor, or any combination thereof.

The system 10 may also include other features to assist in its function and use. For example, FIGS. 1A and 1B represent the housing 12 as including a pair of handles 14 affixed thereto that are configured to promote ease of transporting the housing 12. As another example, the system 10 may include a port on an exterior of the housing 12 configured to couple with an external or integral electrical cord for recharging an internal battery pack and/or powering the system 10 (in which case a battery pack may be unnecessary).

The system 10 may include various controls to activate the components and operations of the system 10 such that the contents of the housing 12 may be dispensed, the light sources 20 activated, and/or any other operations are initiated. In certain embodiments, the system 10 may include an interactive electronic display that shows information such as a counter for quantities of the sacramental elements 24 stored in the system 10 and/or dispensed therefrom, and/or remaining battery power.

Figure 2A:
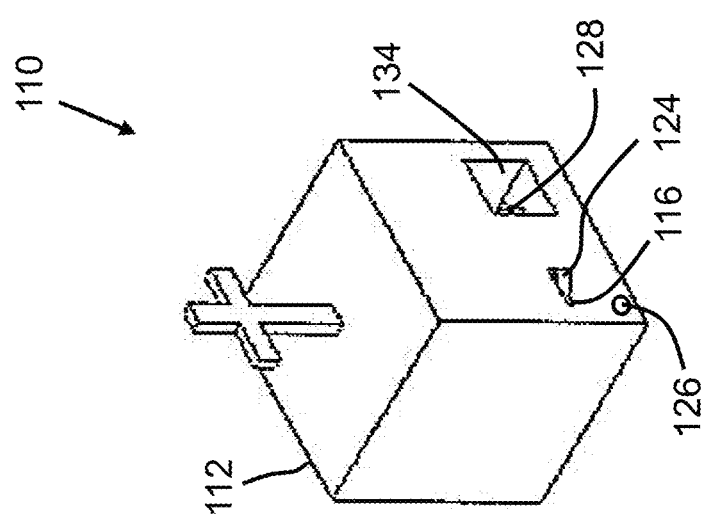

FIGS. 2A, 2B, and 2C represent a second embodiment of a dispensing system 110 for dispensing sacramental elements. In view of similarities between the first and second embodiments (e.g., systems 10 and 110, respectively), the following discussion of FIGS. 2A through 2C will focus primarily on aspects of the second embodiment that differ from the first embodiment represented in FIGS. 1A through 1D in some notable or significant manner. Other aspects of the second embodiment not discussed in any detail can be, in terms of structure, function, materials, etc., essentially as was described for the first embodiment.

The dispensing system 110 is shown in FIGS. 2A through 2C as including a housing 112 having a compartment 122 therein configured to store sacramental elements and one or more dispensing devices within the compartment 122 configured to controllably dispense a predetermined quantity or volume of the sacramental elements, either from an outlet or slot 116 or a spout 128. FIGS. 2A and 2B represent exterior views of the housing 112 and FIG. 2C represents a cutaway rear view of the housing 12 showing exemplary dispensing devices 130 and 132 configured to store and dispense solid sacramental elements, liquid sacramental elements, and containers, respectively.

The dispensing device 130 may dispense a solid sacramental element 124 (e.g., a communion wafer) through the slot 116 in the housing 112. In certain embodiments, the sacramental element 124 is dispensed by the dispensing device 130 such that the sacramental element 124 only partially protrudes from the slot 116 to promote ease of retrieval, as represented in FIG. 2A. In such embodiments, the sacramental element 124 may be automatically partially presented or exposed, for example, upon turning on the system 110, or in response to an interaction between an individual and an activation device 126 of the system 110. With the sacramental element 124 partially exposed within the slot 116, an individual may grasp and pull the sacramental element 124 therefrom. After an individual has retrieved the sacramental element 124, the dispensing device 130 within the housing 112 may replace the retrieved sacramental element 124 with an additional, partially exposed sacramental element 124 of the same type from within the compartment 122 either automatically in response to detecting that the sacramental element 124 has been retrieved or in response to a later interaction between an individual and the activation device 126. The solid sacramental elements 124 may be stored and dispensed with the dispensing device 130 with or without the use of individual packaging.

The dispensing device 132 is represented as comprising a container that contains and dispenses a liquid sacramental element (e.g., wine, juice, or other potable liquid) through the spout 128, which is located within a niche 134 within the housing 112. The container may be, for example, a reusable container or an aseptic, single-use container or bag. To retrieve the liquid sacramental element, an individual may manually place a cup 136 on a surface within the niche 134 below the spout 128. The liquid sacramental element may then be dispensed from the spout 128 automatically when the cup 136 is detected by a sensor, or in response to an interaction between the individual and the activation device 126 of the system 110. In certain embodiments, the dispensing device 132 may dispense the cup 136 such that the cup 136 rests on the surface within the niche 134 below the spout 128. In such embodiments, the cup 136 may be dispensed automatically upon sensing with a sensor that there is not a cup 136 currently located on the surface within the niche 134, or in response to an interaction between the individual and the activation device 126.

Once the cup 136 has been filled with a predetermined volume of the liquid sacramental element from the spout 128, the filled cup 136 may be manually retrieved by an individual. In this manner, a consistent, predetermined volume of the liquid sacramental element may be repeatedly dispensed to consecutive individuals.

As discussed previously in relation to the first embodiment of FIGS. 1A through 1D, the system 110 may include means for sanitizing, for example, UV-C-emitting light sources (not shown), the sacramental elements stored in the compartment 122, packaging of the sacramental elements, the cups 136, and/or other internal components and surfaces of the housing 112. Further, the housing 112 may include features such as those discussed previously for promoting exposure to the UV-C radiation or other sanitation elements. The system 110 may include other features as well, including but not limited to handles, electrical cords and/or ports for coupling thereto, internal battery packs, and various controls to activate and/or control the components and operations of the system 110.

FIGS. 3A through 4C schematically represent aspects of a third embodiment of a dispensing system 210 for dispensing sacramental elements. In view of similarities between the previous embodiments (e.g., dispensing systems 10 and 110), the following discussion of FIGS. 3A through 4C will focus primarily on aspects of the third embodiment that differ from the first and second embodiments represented in FIGS. 1A through 2C in some notable or significant manner. Other aspects of the third embodiment not discussed in any detail can be, in terms of structure, function, materials, etc., essentially as was described for the first and/or second embodiments.

The dispensing system 210 includes a housing 212 (only partially shown) having a compartment therein configured to store the sacramental elements and one or more dispensing devices within the compartment configured to controllably dispense a predetermined quantity or volume of the sacramental elements, either from an outlet or slot 216 or within a niche 234.

The system 210 may dispense a solid sacramental element 224 (e.g., a communion wafer) from the slot 216 in a manner identical or similar to as described previously in reference to the system 110. As represented in FIGS. 3A and 3B, an individual may retrieve a partially protruding solid sacramental element 224 from the slot 216, and then a dispensing device (not shown) within the housing 212 may automatically replace the retrieved solid sacramental element 224 with an additional solid sacramental element 224 of the same type from within the compartment. Alternatively, as described in reference to the system 110, the system 210 may dispense and dispense the solid sacramental element 224 from the slot 116 partially or entirely in response to an interaction between the individual and an activation device.

Figures 4A, 4B, 4C:
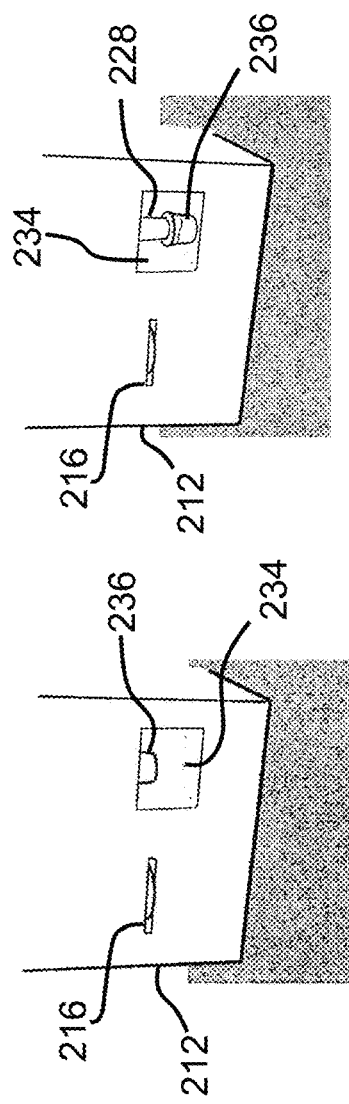
FIGS. 4A, 4B, and 4C represent partial perspective views depicting another method of using the dispensing system of FIGS. 3A and 3B in accordance with certain nonlimiting aspects of the invention.

In FIGS. 4A and 4B, a prepackaged, sealed container (cup) 236 containing a predetermined volume of a liquid sacramental element (i.e., wine, juice, or other potable liquid) therein is dispensed and located on a surface within the niche 234. The sealed cup 236 may be dispensed automatically upon sensing with a sensor that there is not a sealed cup 236 currently located on the surface within the niche 234, or in response to an interaction between the individual and an activation device.

FIG. 4B represents the sealed cup 236 as being lowered with an arm 228. The arm 228 may hold the sealed cup 236 while lowering the cup 236 to release it once the cup 236 is located on or adjacent the surface within the niche 234, and then return to a raised position and/or retrieve and hold an additional sealed cup 236 intended to be dispensed in the future. The arm 228 may hold the sealed cup 236 with a suction force (i.e., vacuum), with mechanical grasping components, or any other suitable means. In certain embodiments, the arm 228 may be replaced with a chute configured to individually dispense the sealed containers 222 onto the surface of the niche 234.

Once a sealed cup 236 has been located onto the surface of the niche 234 and released, the cup 236 may be manually retrieved by an individual, as represented in FIG. 4C. In this manner, a consistent, predetermined volume of the liquid sacramental element may be dispensed to each individual.

As discussed previously in relation to the previous embodiments, the system 210 may include means for sanitizing, for example, UV-C-emitting light sources (not shown) the sacramental elements stored in the housing 212, packaging containing sacramental elements, and/or other internal components and surfaces of the housing 212. Further, the housing 212 may include features such as those discussed previously for promoting exposure to the UV-C radiation or other sanitation elements. The system 210 may include other features as well, including but not limited to handles, electrical cords and/or ports for coupling thereto, internal battery packs, and various controls to activate and/or control the components and operations of the system 210.

Figure 5:
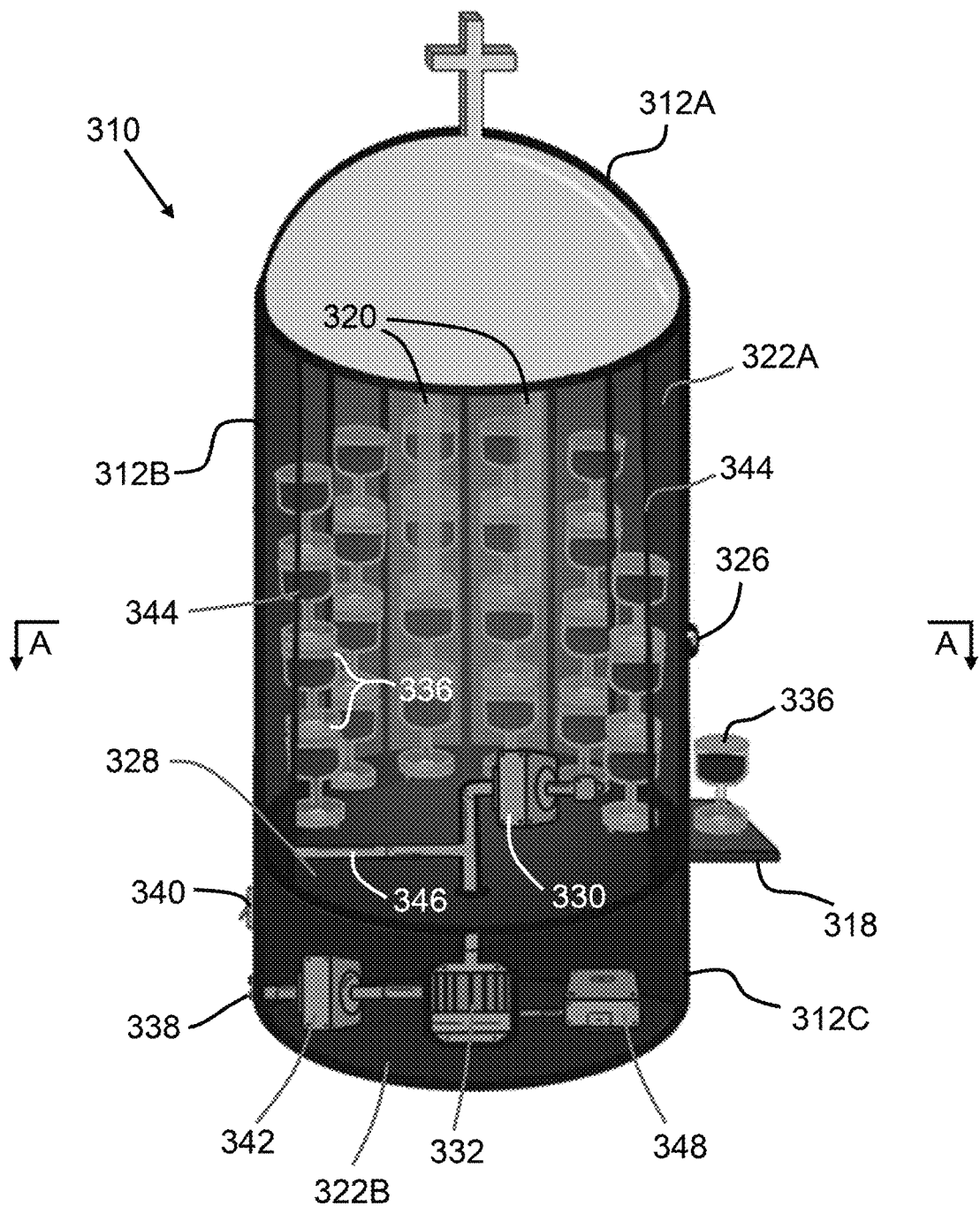
FIG. 5 represents a fourth nonlimiting embodiment of a dispensing system in accordance with certain aspects of the invention. Certain components of the dispensing systems are represented as transparent for convenience.
Figure 6:
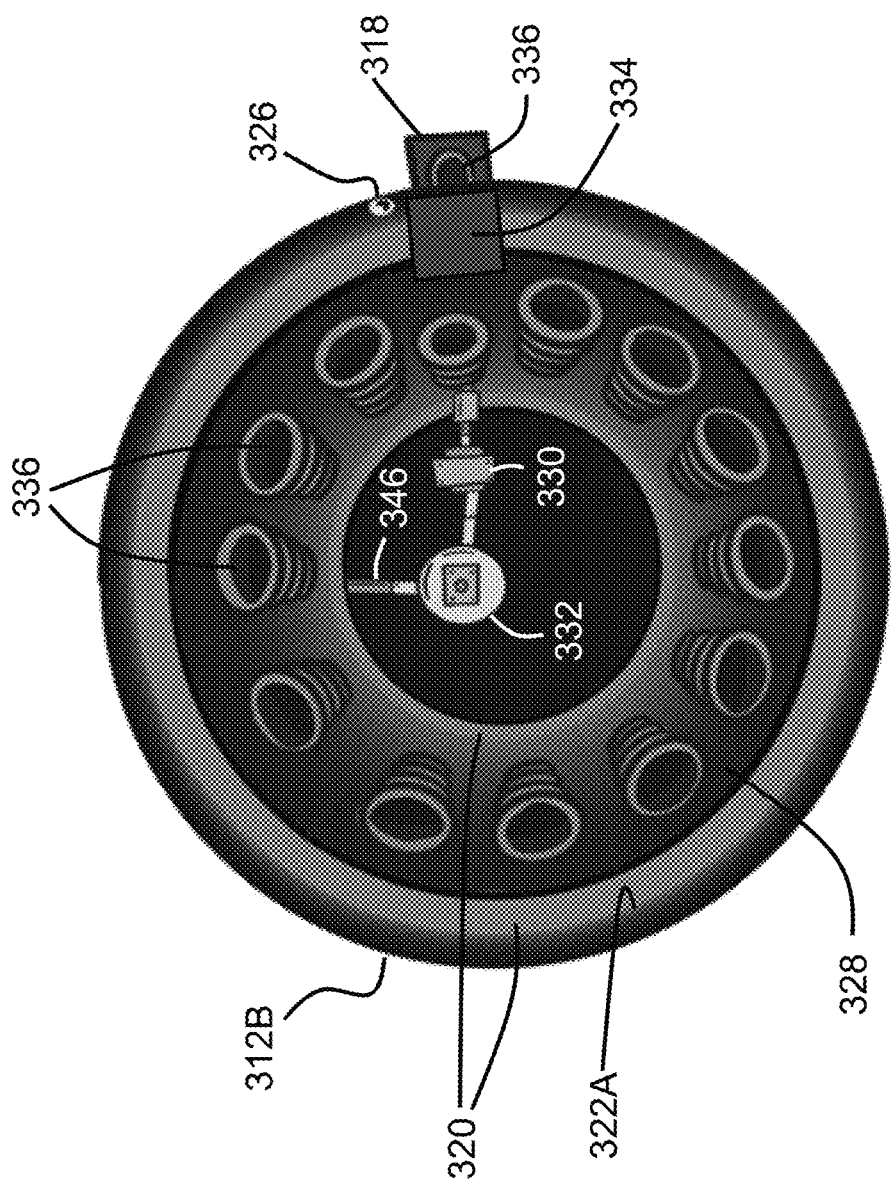
FIG. 6 represents a cutaway, top view of section A-A of the dispensing system of FIG. 5.

FIGS. 5 and 6 schematically represent aspects of a fourth embodiment of a dispensing system 310 for dispensing sacramental elements. In view of similarities between the previous embodiments (i.e., systems 10, 110, and 210), the following discussion of FIGS. 5 and 6 will focus primarily on aspects of the fourth embodiment that differ from the first and second embodiments represented in FIGS. 1A through 4C in some notable or significant manner. Other aspects of the third embodiment not discussed in any detail can be, in terms of structure, function, materials, etc., essentially as was described for the first, second, and/or third embodiments.

The system 310 includes a housing 312 configured to store a quantity of prepackaged, sealed cups (represented as chalices) 336 containing therein a predetermined volume of a liquid sacramental element (e.g., wine, juice, or other potable liquid) in a first compartment 322A thereof and a solid sacramental element (e.g., communion wafer) in a second compartment 322B thereof. For convenience, the housing 312 will be described as having a top section 312A, a middle section 312B that generally encloses the first compartment 322A, and a bottom section 312C that generally encloses the second compartment 322B.

The system 310 is configured to store a quantity of the sealed chalices 336 within the first compartment 322A of the housing 312 for individual distribution. The sealed chalices 336 may be stored in a carriage 344 located in the compartment 322A and configured to retain and transport the chalices 336. In this embodiment, the carriage 344 includes vertical channels defined by rods, guides, chutes, or similarly functional structures configured to maintain the sealed chalices 336 in stacks within the housing 312. Preferably, the stacks of sealed chalices 336 are located on a carousel 328 that is configured to simultaneously move the carriage 344 and all of the sealed chalices 336 therein about an inner circumference of the compartment 322A. Various components and systems may be used to controllably rotate the carousel 328. For example, FIGS. 5 and 6 represent the system 310 as including a mechanical arm 346 that is coupled to the carousel 328. The mechanical arm 346 is configured to rotate about a central axis of the middle section 312B and selectively rotate the carousel 328 and the carriage 344 thereon within the compartment 322A. Movement of the mechanical arm 346 is activated by an electric motor 332, which is controlled by a control device 348. The carousel 328 may be moved automatically, for example, in response to a vertical channel being empty of sealed chalices 336, or in response to an interaction between an individual and an activation device 326. These components may be powered by a battery pack 342 or an external source of power. Such components are known in the art and therefor will not be discussed in further detail herein.

In order to dispense the sealed chalices 336, the carriage 344 may be rotated such that a selected one of the vertical stacks of the sealed chalices 336 is aligned with a niche 334 (FIG. 6) that provides access to the compartment 322A containing the carousel 328 and its chalices 336. Similar to the first embodiment represented in FIGS. 1A through 1D, the niche 334 may be covered with a cover panel 318 configured to selectively open and/or close to provide and/or restrict access to the niche 334. Once a desired vertical stack of the sealed chalices 336 is aligned with the niche 334, the system 310 may dispense individual ones of the sealed chalices 336 from the selected vertical stack automatically or upon interaction between an individual and the activation device 326 of the system 310.

In FIGS. 5 and 6, the system 310 is represented as including the activation device 326 configured to detect the presence of an individual in proximity thereto. Upon detection by the activation device 326, the cover panel 318 opens to uncover the niche 334 and remains open as the carriage 344 dispenses a lowermost chalice 336 within the selected stack of chalices 336 aligned with the niche 334. The lowermost chalice 336 may be dispensed from the niche 334 with an electrical pusher device 330 driven by the electric motor 332 and configured to physically contact and push the chalice 336 from the carriage 344, through the niche 334, and onto an upper surface of the cover panel 318.

As the pusher device 330 retracts into the compartment 322A, sealed chalices 336 in the stack aligned with the niche 334 will fall or slide downwards filling the vacancy left by the dispensed chalice 336. Therefore, a new lowermost chalice 336 will be located in front of the pusher device 330 ready to be translated into the niche 334 as desired. The pusher device 330 may be activated by the control device 348 and mechanically moved via an electric motor (not shown) or solenoid device (not shown) which may be powered with the battery pack 342 or an external source of power.

Once the dispensed chalice 336 is located on the cover panel 318, an individual may manually retrieve the chalice 336. Thereafter, the cover panel 318 may close and seal the niche 334. This process may be repeated as multiple individuals interact with the activation device 326 to receive their respective chalices 336. Preferably, the cover panel 318 opens and closes between dispensing of each one of the chalice 336.

Various alternative structures may be substituted for the carriage 344 described previously that includes vertical channels with stacks of sealed chalices 336. For example, the carriage 344 may instead include guide brackets spaced apart in a manner configured to allow the sealed chalices 336 to slide toward the niche 334. In other embodiments, the carriage 344 may include a rail system where shoulders of the sealed chalices 336 glide along rails of the rail system toward the niche 334. In yet other embodiments, the carriage 344 may include a helical (helicoid) ramp encircling a central vertical axis of the system 310. In such embodiments, the ramp may store the sealed chalices 336 in a consecutive arrangement such that the chalices 336 are biased (via gravity or a biasing member) and directed to travel downwards on the ramp toward the niche 334. In the alternative embodiments noted above, the sealed chalices 336 may travel along the guide brackets, rail system, or ramp at a rate corresponding to the rate of dispensing through the niche 334.

As discussed previously in relation to the previous embodiments, the system 310 may include means for sanitizing, for example, light sources that emit UV-C radiation, the sealed chalices 336 stored in the compartment 322A and/or other internal components and surfaces of the housing 312. Further, the housing 312 may include features such as those discussed previously for promoting exposure to the UV-C radiation or other sanitation elements.

For example, FIGS. 5 and 6 represent the system 310 as including UV-C light sources 320 mounted within the compartment 322A. In the example shown in FIG. 6, one or more light sources 320 are mounted along the interior wall of the compartment 322A and surround the carousel 328, and one or more light sources 320 are mounted centrally within the compartment 322A and are surrounded by the carousel 328. The light emitted from the UV-C light sources 320 irradiate exterior surfaces of the sealed chalices 336 stored in the housing 312 as well as certain internal components of the housing 312 or portions thereof (collectively referred to as the contents of the housing 312). Other light sources may be located in various locations within the housing 312 to maximize irradiation of the contents of the housing 312 by UV-C radiation.

The system 310 may include other features as well, including but not limited to handles, electrical cords and/or ports for coupling thereto, and various controls to activate and/or control the components and operations of the system 310. As examples, FIGS. 5 and 6 represent the system 310 as including a charging port 338 for charging the battery pack 342 and a switch 340 for turning the system 310 on and off.

Various materials may be used in construction of the systems 10, 110, 210, and 310, and their components including but not limited to various metallic materials (e.g., stainless steel or aluminum), polymeric materials, composites, and natural woods. The housings 12, 112, 212, and 312 may include various aesthetic features, such as religious symbols (e.g., crosses represented in the FIGS. 1A-1C, 2A-2C, and 5). Preferably, components that contact the sacramental elements or packaging thereof are formed of materials with relatively low coefficients of friction to promote sliding of the contents. Internal components and surfaces may be formed of reflective materials, polished, and/or coated with reflective materials (e.g., silver chrome or bronze alloys) to promote reflection of the UV-C radiation within the housings 12, 112, 212, and 312.

The systems 10, 110, 210, and 310, may be produced in various shapes and sizes, and may include features specific to certain applications. For example, the dispensing device and/or the stored sacramental elements may be housed in a pre-filled, self-contained body that is removable such that the contents of the housings 12, 112, 212, and/or 312 may be quickly replaced. In other embodiments, the systems 10, 110, 210, and 310 may include a modular configuration wherein the housings 12, 112, 212, and/or 312 include modular components, for example, similar to the top section 312A, the middle section 312B, and the bottom section 312C of FIG. 5, that are functionally but releasably coupled together. Such arrangement may promote ease of replacing the sacramental elements stored therein and/or portions of the systems 10, 110, 210, and/or 310 that require replacement. In addition, such modular structures may be configured to receive additional sections, for example, to provide additional capacity of the sacramental elements or increased output through additional outlets. For example, the fourth embodiment of FIGS. 5 and 6 may be configured to stack additional middle sections 312B between the top section 312A and a bottom section 312C. In yet other embodiments, the systems 10, 110, 210, and 310 or portions thereof may be removably stored in a decorative housing such that the visual aesthetics may be chosen by the end user. Such decorative housings may be specific to a theme, such as religious symbols for use in a place of worship, or may be customizable by the end user.

While aspects of the embodiments described herein have been discussed in relation to the Christian rite of Communion and the distribution of sacramental elements therefor, it should be understood that the invention is not limited to such applications. The systems 10, 110, 210, 310, and variations thereof may be used for various applications such as, but not limited to, distribution of sacramental elements or other items associated with various religious ceremonies, distribution of consumer products, and distribution of medications. In certain embodiments, the systems 10, 110, 210, and 310 may include features that allow for individuals to provide payment for items prior to dispensing such items. In some embodiments, the systems 10, 110, 210, and 310 may be configured to track and/or measure the items dispensed. In embodiments related to the distribution of medications (e.g., hospitals, senior centers, prisons, etc.), the systems 10, 110, 210, and 310 may be configured to verify identities of users, verify prescriptions, measure doses, and track and store information relating to dispensed items. The systems 10, 110, 210, and 310 may be further configured to physically or remotely connect with other devices to provide additional functionality and/or transmit stored data (e.g., remaining contents, distributed contents, etc.).

While the invention has been described in terms of specific embodiments, it is apparent that other forms could be adopted by one skilled in the art. For example, the systems 10, 110, 210, and 310 and their components could differ in appearance and construction from the embodiments described herein and shown in the drawings, functions of certain components of the systems 10, 110, 210, and 310 could be performed by components of different construction but capable of a similar (though not necessarily equivalent) function, and various materials could be used in the fabrication of the systems 10, 110, 210, and 310 and/or their components. In addition, the invention encompasses additional embodiments in which one or more features or aspects of different disclosed embodiments may be combined or eliminated. Therefore, the scope of the invention is to be limited only by the following claims.

The invention claimed is:
1. A system for dispensing items, the system comprising:
a housing having a compartment therein configured to store a quantity of items;
a dispensing device configured to dispense at least one of the items from the housing to an individual;

an activation device configured to activate the dispensing device to dispense the at least one item from the housing in response to an interaction with the individual;

an outlet in the housing through which the items may be individually dispensed from the housing by the dispensing device; and one or more light sources that emit UV-C radiation within the housing and irradiate exterior surfaces of the items or packaging of the items with the UV-C radiation;

wherein the dispensing device includes:

a carriage configured to retain the items;

a pusher device configured to physically contact and push the items individually from the carriage and through the outlet of the housing;

a control device configured to activate the pusher device in response to the individual's interaction with the activation device; and means for powering the pusher device and the control system.

2. The system of claim 1, wherein the housing includes modular components that are configured to be functionally coupled together, wherein the items are stored in a first of the modular components, the system comprising at least one additional modular component identical to the first modular component and configured to be coupled with the first modular component to increase the capacity of the items stored within the housing.

3. The system of claim 1, wherein the items are sacramental elements for use during the Christian rite of Communion.

4. The system of claim 1, wherein the at least one item is dispensed from the dispensing device in response to an individual's direct, physical interaction with the activation device.

5. The system of claim 1, wherein the at least one item is dispensed from the dispensing device automatically in response to the activation device detecting the individual with an activation device.

6. The system of claim 1, wherein the items include a plurality of solid items, and the dispensing device is configured to dispense one of the plurality of solid items to the individual in response to the individual's interaction with the activation device.

7. The system of claim 1, wherein the items include a volume of liquid, and the dispensing device is configured to dispense a predetermined volume of the liquid to the individual in response to the individual's interaction with the activation device.

8. The system of claim 1, wherein the items includes a plurality of sealed containers each comprising a solid item, a predetermined volume of a liquid, or both.

9. The system of claim 8, wherein the liquid is dispensed to the individual from the dispensing device in a liquid container.

10. The system of claim 1, wherein the carriage includes a multiple vertical channels having structural features configured to maintain the items in stacks.

11. The system of claim 1, further comprising a cover panel that covers the outlet, wherein the cover panel is configured to open to uncover the outlet when the dispensing device dispenses the at least one sacramental element, and close to cover the outlet after the at least one sacramental element has been dispensed.

12. A system for dispensing items, the system comprising:
a housing having a compartment therein configured to store a quantity of items;
a dispensing device configured to dispense at least one of the items from the housing to an individual;
an activation device configured to activate the dispensing device to dispense the at least one item from the housing in response to an interaction with the individual;
an outlet in the housing through which the items may be individually dispensed from the housing by the dispensing device; and
one or more light sources that emit UV-C radiation within the housing and irradiate exterior surfaces of the items or packaging of the items with the UV-C radiation;
wherein the dispensing device is a self-contained body that is configured to be pre-filled with the items and be selectively inserted into and removed from the housing.

13. A method of distributing items, the method comprising:
providing a system comprising a housing having a compartment therein configured to store a quantity of the items;
sensing an interaction between an individual and an activation device of the system;
activating a dispensing device of the system to dispense at least one of the items from the housing through an outlet of the housing in response the interaction between the individual and the activation device;
irradiating exterior surfaces of the items or packaging of the items with UV-C radiation emitted from one or more light sources within the housing; and
removing a first self-contained body comprising the dispensing device from the housing and then replacing the first self-contained body with a second self-contained body comprising a second dispensing device identical to the first dispensing device and pre-filled with additional items.

14. The method of claim 13, wherein the items are sacramental elements and the method includes dispensing the sacramental elements during the Christian rite of Communion.

15. The method of claim 13, wherein the interaction sensed by the activation device is a direct, physical contact between the individual and a component of the activation device.

16. The method of claim 13, wherein the interaction sensed by the activation device is a proximity of the individual to the system as detected by an activation device of the activation device.

17. The method of claim 13, further comprising opening a cover panel to uncover the outlet when the dispensing device dispenses the at least one item, and closing the cover panel to cover the outlet after the at least one item has been dispensed.

18. The method of claim 13, further comprising:
assembling the housing by functionally coupling modular components together, wherein the items are stored in a first of the modular components; and
adding at least one additional modular component to the housing that is identical to the first modular component and thereby increasing the capacity of the items stored within the housing.

* * * * *